US008116868B2

(12) United States Patent
Haefner

(10) Patent No.: US 8,116,868 B2
(45) Date of Patent: Feb. 14, 2012

(54) IMPLANTABLE DEVICE WITH CARDIAC EVENT AUDIO PLAYBACK

(75) Inventor: Paul Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 880 days.

(21) Appl. No.: 10/801,139

(22) Filed: Mar. 15, 2004

(65) Prior Publication Data
US 2004/0230249 A1 Nov. 18, 2004

Related U.S. Application Data

(60) Provisional application No. 60/462,272, filed on Apr. 11, 2003.

(51) Int. Cl.
*A61N 1/365* (2006.01)
(52) U.S. Cl. .......................... 607/17; 600/513; 600/528
(58) Field of Classification Search .................. 607/17; 600/513, 528
See application file for complete search history.

(56) References Cited

U.S. PATENT DOCUMENTS

| 4,220,160 A | * | 9/1980 | Kimball et al. ............... 600/528 |
| 4,362,164 A | * | 12/1982 | Little et al. .................... 600/382 |
| 4,562,841 A | | 1/1986 | Brockway et al. |
| 4,614,192 A | * | 9/1986 | Imran et al. ..................... 607/5 |
| 4,763,646 A | * | 8/1988 | Lekholm ......................... 607/14 |
| 4,867,163 A | * | 9/1989 | Schaldach ....................... 607/22 |
| 4,953,551 A | | 9/1990 | Mehra et al. |
| 5,010,889 A | * | 4/1991 | Bredesen et al. ............. 600/528 |
| 5,036,849 A | | 8/1991 | Hauck et al. |
| 5,133,353 A | | 7/1992 | Hauser |
| 5,170,784 A | | 12/1992 | Ramon et al. |
| 5,179,945 A | | 1/1993 | Van Hofwegen et al. |
| 5,203,348 A | | 4/1993 | Dahl et al. |
| 5,209,229 A | | 5/1993 | Gilli |
| 5,230,337 A | | 7/1993 | Dahl et al. |
| 5,261,400 A | | 11/1993 | Bardy |
| 5,284,136 A | | 2/1994 | Hauck et al. |
| 5,292,338 A | | 3/1994 | Bardy |

(Continued)

FOREIGN PATENT DOCUMENTS

EP 0 532 149 3/1993

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner* — Michael Kahelin
(74) *Attorney, Agent, or Firm* — Hollingsworth & Funk, LLC

(57) ABSTRACT

Cardiac monitoring and stimulation methods and systems provide audio playback of cardiac events and transthoracic monitoring and therapy. A medical system includes a housing and electrodes configured for sensing cardiac electrical activity. Another sensor may be configured to sense heart movement and produce a signal in response, such as an audio signal. Memory stores the audio signal and the cardiac electrical signal. A controller and communications circuitry telemeter the cardiac electrical signal and the audio signal to a patient-external device. Energy delivery circuitry may deliver cardiac therapy. The device may further include a patient actuatable trigger configured to communicate to the controller via the communications circuitry. The controller may initiate storing of the cardiac electrical signal and the audio signal in response to the trigger. The patient-external device may further include a storage media.

9 Claims, 8 Drawing Sheets

U.S. PATENT DOCUMENTS

| | | | |
|---|---|---|---|
| 5,300,106 A | 4/1994 | Dahl et al. | |
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |
| 5,321,618 A * | 6/1994 | Gessman | 607/5 |
| 5,331,966 A | 7/1994 | Bennett et al. | |
| H1347 H | 8/1994 | Greeninger et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,376,106 A | 12/1994 | Stahmann et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,464,434 A | 11/1995 | Alt | |
| 5,468,254 A | 11/1995 | Hahn et al. | |
| 5,496,361 A * | 3/1996 | Moberg et al. | 607/122 |
| 5,531,779 A | 7/1996 | Dahl et al. | |
| 5,545,202 A | 8/1996 | Dahl et al. | |
| 5,549,652 A | 8/1996 | McClure et al. | |
| 5,603,732 A | 2/1997 | Dahl et al. | |
| 5,620,466 A | 4/1997 | Haefner et al. | |
| 5,634,938 A | 6/1997 | Swanson et al. | |
| 5,641,326 A | 6/1997 | Adams | |
| 5,662,688 A | 9/1997 | Haefner et al. | |
| 5,697,953 A | 12/1997 | Kroll et al. | |
| 5,702,427 A | 12/1997 | Ecker et al. | |
| 5,704,365 A | 1/1998 | Albrecht et al. | |
| 5,724,984 A | 3/1998 | Arnold et al. | |
| 5,737,429 A * | 4/1998 | Lee | 381/67 |
| 5,827,326 A | 10/1998 | Kroll et al. | |
| 5,888,187 A * | 3/1999 | Jaeger et al. | 600/23 |
| 5,895,414 A | 4/1999 | Sanchez-Zambrano | |
| 5,916,243 A | 6/1999 | KenKnight et al. | |
| 5,935,081 A * | 8/1999 | Kadhiresan | 600/513 |
| 5,941,829 A * | 8/1999 | Saltzstein et al. | 600/509 |
| 5,957,956 A | 9/1999 | Kroll et al. | |
| 6,044,298 A | 3/2000 | Salo et al. | |
| 6,055,454 A | 4/2000 | Heemels | |
| 6,148,230 A | 11/2000 | KenKnight | |
| 6,236,889 B1 | 5/2001 | Soykan et al. | |
| 6,280,462 B1 | 8/2001 | Hauser et al. | |
| 6,409,675 B1 | 6/2002 | Turcott | |
| 6,415,174 B1 | 7/2002 | Bebehani et al. | |
| 6,438,410 B2 | 8/2002 | Hsu et al. | |
| 6,477,406 B1 * | 11/2002 | Turcott | 600/518 |
| 6,480,733 B1 | 11/2002 | Turcott | |
| 6,491,639 B1 | 12/2002 | Turcott | |
| 6,512,940 B1 | 1/2003 | Brabec et al. | |
| 6,522,915 B1 | 2/2003 | Ceballos et al. | |
| 6,564,106 B2 | 5/2003 | Guck et al. | |
| 6,607,509 B2 | 8/2003 | Bobroff et al. | |
| 6,615,083 B2 | 9/2003 | Küpper | |
| 6,622,046 B2 | 9/2003 | Fraley et al. | |
| 6,643,548 B1 * | 11/2003 | Mai et al. | 607/17 |
| 6,650,940 B1 | 11/2003 | Zhu et al. | |
| 7,035,684 B2 * | 4/2006 | Lee | 600/513 |
| 2002/0026223 A1 * | 2/2002 | Riff et al. | 607/27 |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082658 A1 | 6/2002 | Heinrich et al. | |
| 2002/0091414 A1 | 7/2002 | Bardy et al. | |
| 2002/0095184 A1 | 7/2002 | Bardy et al. | |
| 2002/0103510 A1 | 8/2002 | Bardy et al. | |
| 2002/0107544 A1 | 8/2002 | Ostroff et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0120299 A1 | 8/2002 | Ostroff et al. | |
| 2003/0004546 A1 | 1/2003 | Casey | |
| 2003/0004552 A1 | 1/2003 | Plombon et al. | |
| 2003/0023175 A1 | 1/2003 | Arzbaecher et al. | |
| 2003/0036778 A1 | 2/2003 | Ostroff et al. | |
| 2003/0045904 A1 | 3/2003 | Bardy et al. | |
| 2003/0060723 A1 | 3/2003 | Joo et al. | |
| 2003/0069609 A1 | 4/2003 | Thompson | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |
| 2003/0212436 A1 | 11/2003 | Brown | |
| 2004/0167416 A1 | 8/2004 | Lee | |
| 2004/0167417 A1 | 8/2004 | Schulhauser et al. | |

FOREIGN PATENT DOCUMENTS

WO    WO 92/20402    11/1992

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

\* cited by examiner

IMPLANTABLE DEVICE WITH CARDIAC EVENT AUDIO PLAYBACK

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable cardiac monitoring and stimulation devices and, more particularly, to implantable cardiac monitoring and stimulation devices that incorporate cardiac event audio playback.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to cardiac monitoring and/or stimulation methods and systems that, in general, provide audio playback of cardiac events along with transthoracic monitoring, defibrillation therapies, pacing therapies, or a combination of these capabilities. Embodiments of the present invention are directed to subcutaneous cardiac monitoring and/or stimulation methods and systems that detect and/or treat cardiac activity or arrhythmias.

An embodiment of the invention is direct to a medical system including an implantable housing, with a plurality of implantable electrodes coupled to the housing and configured for sensing cardiac electrical activity. Detection circuitry is provided in the housing and coupled to at least some of the plurality of electrodes, the detection circuitry producing a cardiac electrical signal in response to the sensed cardiac electrical activity. An implantable sensor may be configured to sense movement of a heart and produce a sensor signal in response to the sensed heart movement. Sensor circuitry may be provided in the housing and coupled to the sensor, the sensor circuitry configured to produce an audio signal in response to the sensor signal. Memory is provided in the housing and coupled to the detection circuitry and sensor circuitry, the memory configured to store the audio signal and the cardiac electrical signal. A controller is also provided in the housing and coupled to the memory, detection circuitry, and sensor circuitry. Communications circuitry is provided in the housing and coupled to the controller, the communications circuitry configured to telemeter the cardiac electrical signal and the audio signal to a patient-external device.

Sensors useful with the device include, for example, an accelerometer, a sensor configured to sense pressure waves produced by heart movement, a piezoelectric transducer, and a microphone situated in or on the housing, or in or on a lead. Embodiments of the invention include one or more electrodes configured for subcutaneous, non-intrathoracic placement and/or intrathoracic placement. One or more electrodes may be disposed in or on the housing, and/or supported by a lead configured for subcutaneous, non-intrathoracic placement. A lead may couple one or more of the electrodes to the housing. The device may further include energy delivery circuitry coupled to the controller and at least some of the electrodes. The energy delivery circuitry may be configured to deliver a cardiac therapy. The cardiac therapy may include a cardiac pacing therapy and/or a cardiac defibrillation therapy.

The device may further include a patient actuatable trigger configured to communicate a trigger signal to the controller via the communications circuitry. The controller may initiate storing of the cardiac electrical signal and the audio signal in the memory in response to the trigger signal. The patient-external device may further include a storage media to store the cardiac electrical signal and the audio signal telemetered from the patient-implantable device.

In other embodiments, a medical system in accordance with the present invention is directed to a patient-implantable device having a housing and a plurality of electrodes coupled to the housing and configured for sensing cardiac electrical activity. Detection circuitry is provided in the housing and coupled to at least some of the plurality of electrodes, the detection circuitry producing a cardiac electrical signal in response to the sensed cardiac electrical activity. A sensor configured to sense movement of a heart and produce a sensor signal in response to the sensed heart movement is also provided. Sensor circuitry is provided in the housing and coupled to the sensor, the sensor circuitry configured to produce an audio signal in response to the sensor signal.

Memory is provided in the housing and coupled to the detection circuitry and sensor circuitry. The memory is configured to store the audio signal and the cardiac electrical signal. A controller is provided in the housing and coupled to the memory, detection circuitry, and sensor circuitry. Communications circuitry is provided in the housing and coupled to the controller, the communications circuitry configured to telemeter the cardiac electrical signal and the audio signal to a patient-external device. The patient-external device includes communications circuitry configured to receive the cardiac electrical signal and the audio signal.

A user interface is coupled to the patient-external communications circuitry, the user interface configured for providing a visual output representative of the cardiac electrical signal and an audio output representative of the audio signal. The user interface is configured for providing a visual output representative of the audio signal and an audio output representative of the cardiac electrical signal. A display is configured to display a representation of one or both of the cardiac electrical signal and the audio signal. The display may present one or both of textual and graphical information associated with one or both of the cardiac electrical signal and the audio signal. An audio output device may be included and configured to broadcast the audio signal.

The cardiac electrical signal and the audio signal may be telemetered from the patient-implantable device to the patient-external device in response to a user request, and/or a request by the patient-external device. The patient-external device may further include a storage media to store the cardiac electrical signal and the audio signal telemetered from the patient-implantable device. The patient-external device may further communicate with a server coupled to one or both of the patient-implantable device and the patient-external device.

The cardiac electrical signal and the audio signal may be telemetered from the patient-implantable device to the server and/or communicated from the server to the patient-external device. A time correlation between the cardiac electrical signal and the audio signal may be incorporated in one or both of the signals, or provided in addition to the signals. The user interface may include a speaker configured to broadcast the audio signal and/or a display configured to display a representation of the cardiac electrical signal and indicia indicative of the time correlation.

Methods in accordance with embodiments of the present invention may involve sensing, from within a patient, movement of a heart and producing a sensor signal in response to the sensed heart movement. An audio signal may be produced using the sensor signal. Cardiac electrical activity may be detected and a cardiac electrical signal may be produced in response to the detected cardiac electrical activity. The sensor signal and the cardiac electrical signal may be stored and/or telemetered to a patient-external location such as a patient-external device and/or a server.

The sensor signal and cardiac electrical signal may be telemetered to the patient-external location in response to a trigger signal generated by a patient-actuated device and/or a trigger signal generated by the patient-external system. Suitable sensor signals include accelerometer signals, piezoelectric transducer signals, and microphone output signals, for example. Methods may further involve time correlating the audio signal and the cardiac electrical signal. The cardiac electrical activity may be detected intrathoracically and/or non-intrathoracically. The audio signal may be broadcasted and/or displayed, as well as communicated to a server system. The signals may be telemetered after storage and delay, and/or may be telemetered in real-time.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
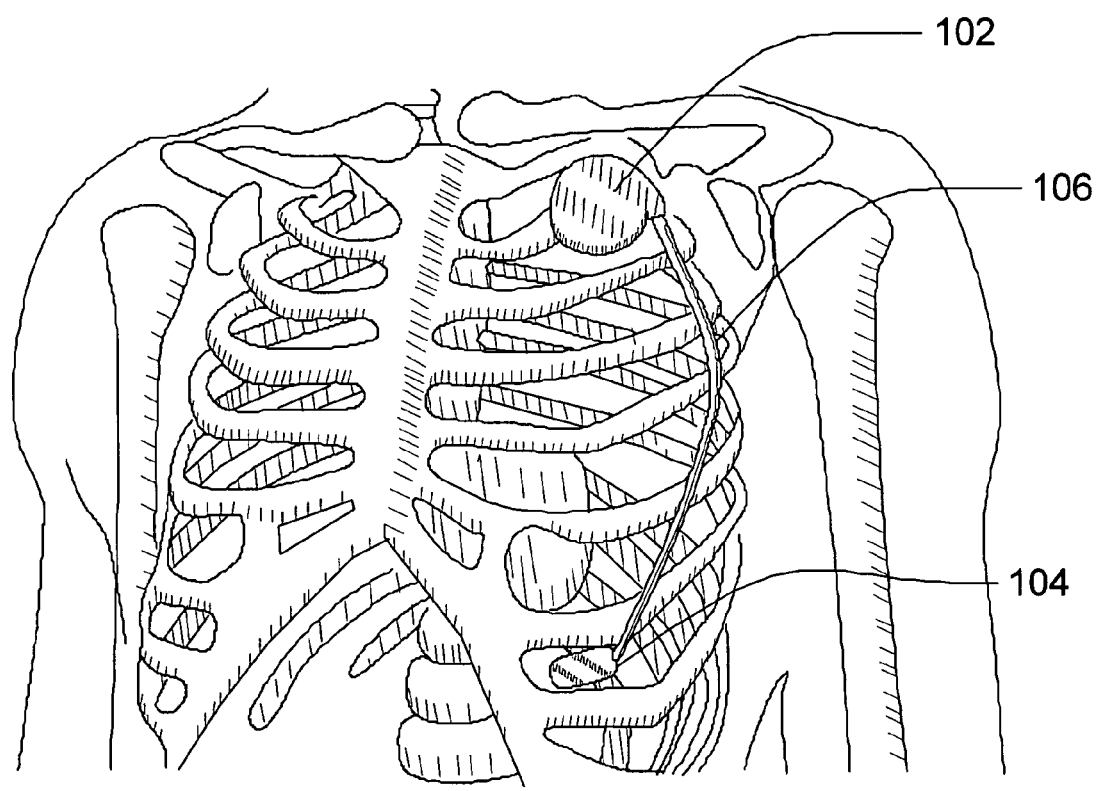
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

Methods and systems incorporating non-electrophysiological signal playback features in accordance with the present invention will be described within the context of an implantable transthoracic cardiac sensing and/or stimulation (ITCS) device as part of an advanced patient management system. The ITCS device may be implanted without the need for intravenous or intrathoracic access, providing a simpler, less invasive implant procedure and minimizing lead and surgical complications. These systems have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS device according to this approach is distinct from conventional approaches in that it may be configured to include a combination of two or more electrode subsystems that are implanted subcutaneously in the anterior thorax. The use of an ITCS device approach is described by way of example only, to provide an embodiment of how audio playback in accordance with the present invention may be implemented. The particular example of an ITCS device is intended to be a non-limiting, non-exhaustive example of devices and systems that may incorporate playback features in accordance with the present invention.

A non-electrophysiological signal playback system in accordance with the present invention may be used with an ITCS device. One such monitoring and/or stimulation device is that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In a further implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from non-electrophysiological signal playback, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference in their respective entireties.

An ITCS device in accordance with the present invention may implement diagnostic and/or monitoring functions as well as provide cardiac stimulation therapy. Exemplary cardiac monitoring circuitry, structures and functionality, aspects of which may be incorporated in an ITCS device of a type that may benefit from non-electrophysiological signal playback in accordance with the present invention, are disclosed in commonly owned U.S. Pat. Nos. 5,313,953; 5,388,578; and 5,411,031, which are hereby incorporated herein by reference.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-electrophysiological information for purposes of enhancing tachyarrhythmia detection and termination. It is understood that configurations, features, and combination of features described in the instant disclosure may be implemented in a wide range of implantable medical devices, and that such embodiments and features are not limited to the particular devices described herein.

Figure 1B:
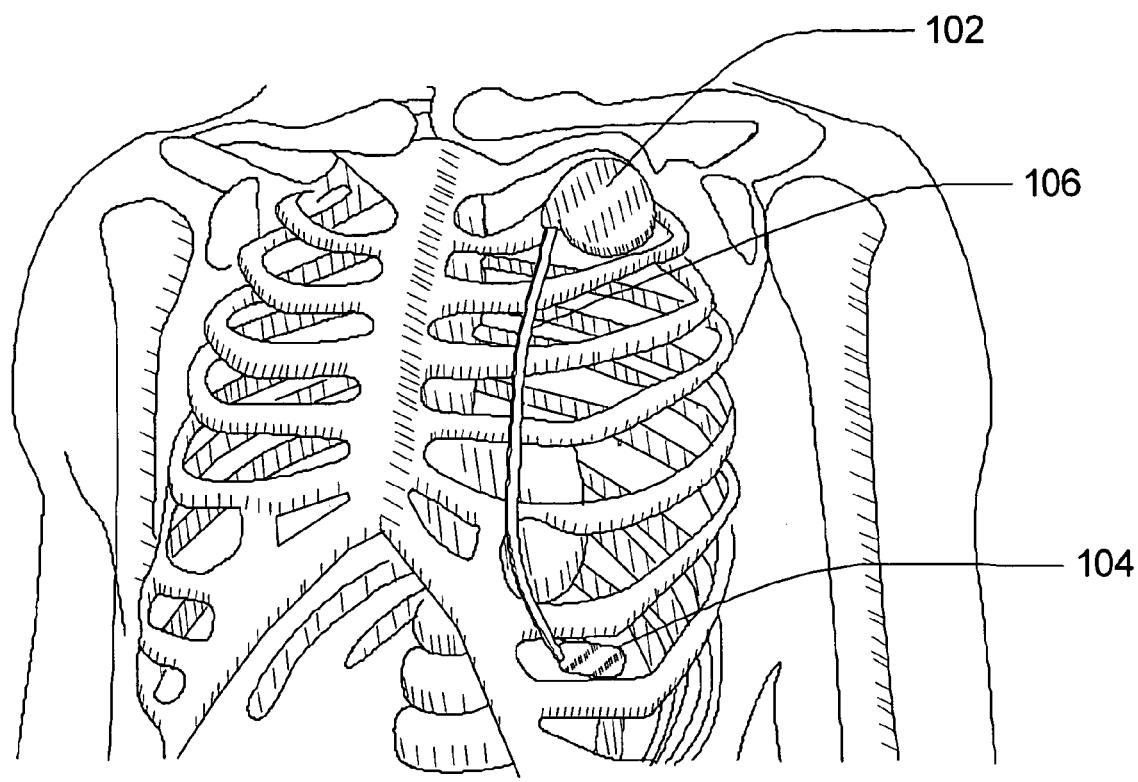

Referring now to FIGS. 1A and 1B of the drawings, there is shown a configuration of an ITCS device having components implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external memory and display, for example. The communications circuitry may also facilitate unidirectional or bidirectional communication with one or more external, cutaneous, or subcutaneous physiologic or non-electrophysiological sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, a rigid electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, a rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Figure 1C:
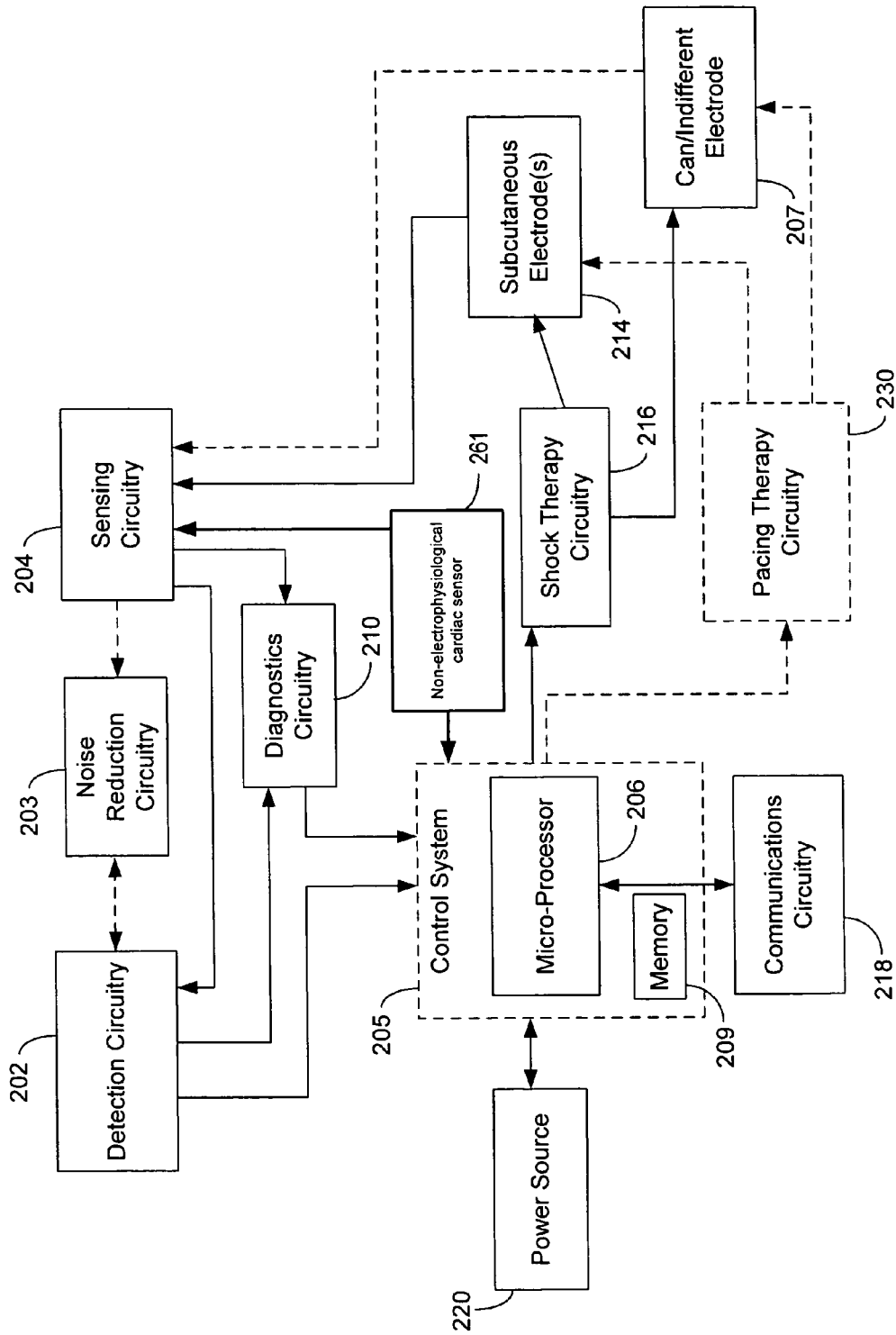
FIG. 1C is a block diagram illustrating various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and/or non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations as well as multi-element electrodes and combinations of electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after sensing circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 1C, the detection circuitry 202 is coupled to, or otherwise incorporates, noise reduction circuitry 203. The noise reduction circuitry 203 operates to improve the signal-to-noise ratio of sensed cardiac signals by removing noise content of the sensed cardiac signals introduced from various sources. Typical types of transthoracic cardiac signal noise includes electrical noise and noise produced from skeletal muscles, for example.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Exemplary arrhythmia detection and discrimination circuitry, structures, and techniques, aspects of which may be implemented by an ITCS device of a type that may benefit from non-electrophysiological signal playback in accordance with the present invention, are disclosed in commonly owned U.S. Pat. Nos. 5,301,677 and 6,438,410, which are hereby incorporated herein by reference.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 is also configured to store historical electrocardiogram (ECG) and non-electrophysiological sensor data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures and functionality, aspects of which may be incorporated in an ITCS device of a type that may benefit from aspects of the present invention are disclosed in commonly owned U.S. Pat. Nos. 5,372,606; 5,411,525; 5,468,254; and 5,634,938, which are hereby incorporated herein by reference.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a transthoracic cardiac monitoring and/or stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C is configured to receive signals from one or more physiologic and/or non-electrophysiological sensors in accordance with embodiments of the present invention. Depending on the type of sensor employed, signals generated by the sensors may be coupled directly to the detection circuitry 202 or indirectly via the sensing circuitry 204. It is noted that certain sensors may transmit sense data to the control system 205 without processing by the detection circuitry 202.

Non-electrophysiological cardiac sensors may be coupled directly to the detection circuitry 202 or indirectly via the sensing circuitry 204. Non-electrophysiological cardiac sensors sense cardiac activity that is non-electrophysiological in nature. Examples of non-electrophysiological cardiac sensors are blood oxygen sensors, blood volume sensors, acoustic sensors and/or pressure transducers, and accelerometers. Signals from these sensors are correlated to cardiac activity, but not derived from electrophysiological sources. A non-electrophysiological cardiac sensor 261 is illustrated in FIG. 1C connected to one or both of the sensing circuitry 204 and the control system 205.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. Communications circuitry 218 may be equipped with a short-range wireless communication interface, such as an interface conforming to a known communications standard, such as Bluetooth or IEEE 802 standards.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, commands and data may be transferred between the ITCS device and the programmer unit both during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive radio frequency energy transmitted by an external radio frequency energy transmitter. The ITCS device may, in addition to a rechargeable power source, include a non-rechargeable battery. It is understood that a rechargeable power source need not be used, in which case a long-life non-rechargeable battery is employed.

Figure 1D:
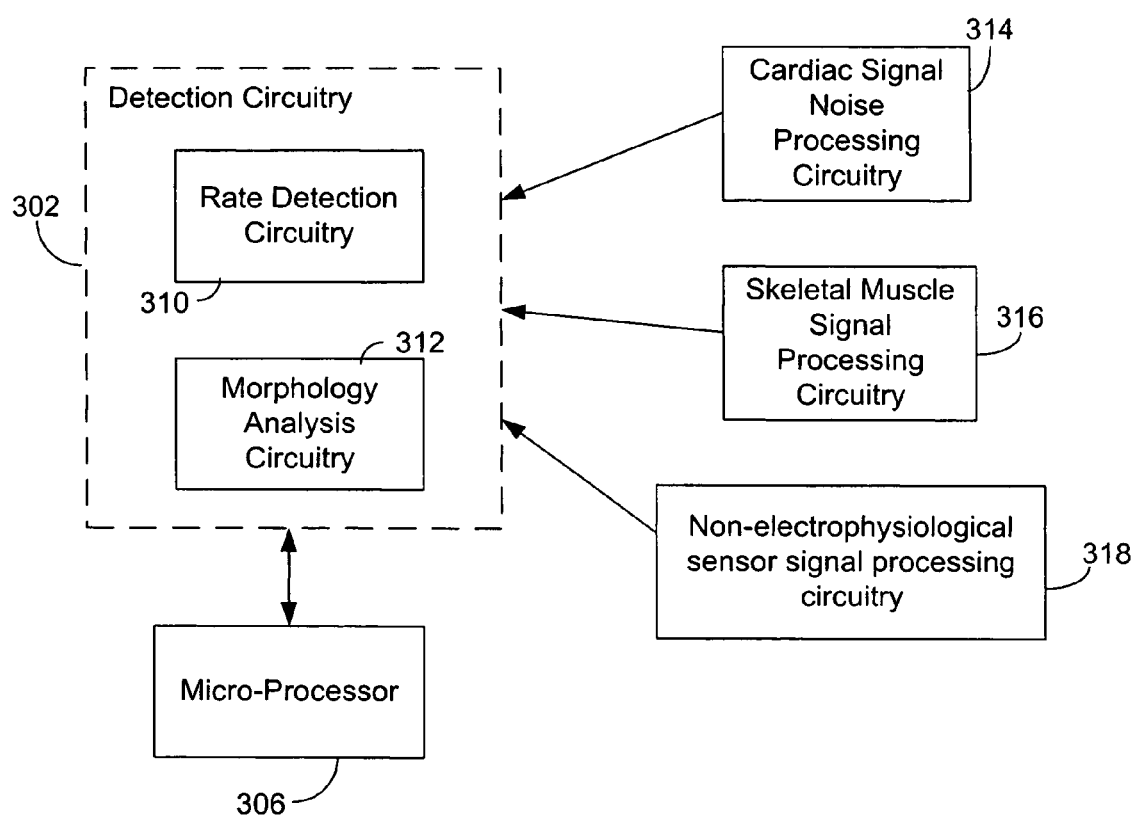
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device, which includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

The detection circuitry 302, which is coupled to a microprocessor 306, may be configured to incorporate, or communicate with, specialized circuitry for processing sensed cardiac signals in manners particularly useful in a transthoracic cardiac sensing and/or stimulation device. As is shown by way of example in FIG. 1D, the detection circuitry 302 may receive information from multiple physiologic and non-electrophysiological sensors. For example, transthoracic acoustics may be monitored using an appropriate acoustic sensor. Heart sounds, for example, may be detected and processed by non-electrophysiological cardiac sensor processing circuitry 318 for a variety of purposes. The acoustics data is transmitted to the detection circuitry 302, via a hardwire or wireless link, and used to enhance cardiac signal detection. For example, acoustic information may be used in accordance with the present invention to help a clinician discriminate normal cardiac sinus rhythm from electrical noise or potentially lethal arrhythmias, such as ventricular tachycardia or ventricular fibrillation.

The detection circuitry 302 may also receive information from one or more sensors that monitor skeletal muscle activity. In addition to cardiac activity signals, transthoracic electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise. Processing circuitry 316 receives signals from one or more skeletal muscle sensors, and transmits processed skeletal muscle signal data to the detection circuitry 302. This data may be used to discriminate normal cardiac sinus rhythm with skeletal muscle noise from cardiac arrhythmias.

The components, functionality, and structural configurations depicted in FIGS. 1A-1E are intended to provide an understanding of various features and combination of features that may be incorporated in a device in accordance with the present invention. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

Figure 1E:
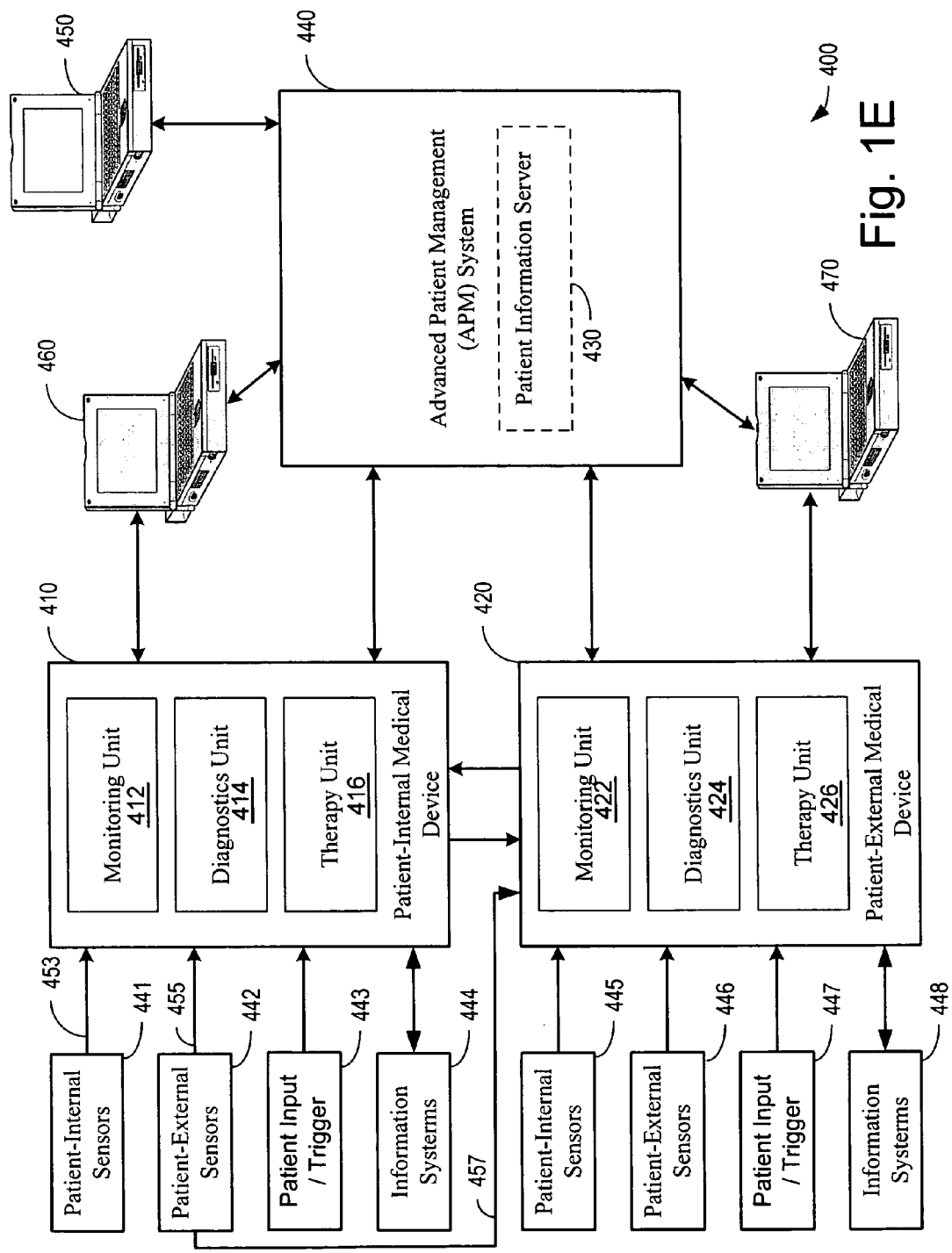
FIG. 1E is a block diagram of a medical system that may be used to implement coordinated patient monitoring, diagnosis, and/or therapy in accordance with embodiments of the present invention.

Referring now to FIG. 1E, the ITCS device may be used within the structure of an advanced patient management (APM) medical system 400. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 1E, the medical system 400 may be used to implement coordinated patient measuring and/or monitoring, diagnosis, and/or therapy in accordance with embodiments of the invention. The medical system 400 may include, for example, one or more patient-internal medical devices 410, such as an ITCS device, and one or more patient-external medical devices 420, such as a monitor or signal display device. Each of the patient-internal 410 and patient-external 420 medical devices may include one or more of a patient monitoring unit 412, 422, a diagnostics unit 414, 424, and/or a therapy unit 416, 426.

The patient-external medical device 420 performs monitoring, and/or diagnosis and/or therapy functions external to the patient (i.e., not invasively implanted within the patient's body). The patient-external medical device 420 may be positioned on the patient, near the patient, or in any location external to the patient.

The patient-internal and patient-external medical devices 410, 420 may be coupled to one or more sensors 441, 442, 445, 446, patient input/trigger devices 443, 447 and/or other information acquisition devices 444, 448. The sensors 441, 442, 445, 446, patient input /trigger devices 443, 447, and/or other information acquisition devices 444, 448 may be employed to detect conditions relevant to the monitoring, diagnostic, and/or therapeutic functions of the patient-internal and patient-external medical devices 410, 420.

The medical devices 410, 420 may each be coupled to one or more patient-internal sensors 441, 445 that are fully or partially implantable within the patient. The medical devices 410, 420 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 441 may be coupled to the patient-internal medical device 410 through one or more internal leads 453. Still referring to FIG. 1E, one or more patient-internal sensors 441 may be equipped with transceiver circuitry to support wireless communications between the one or more patient-internal sensors 441 and the patient-internal medical device 410 and/or the patient-external medical device 420.

The patient-external sensors 442 may be coupled to the patient-internal medical device 410 and/or the patient-external medical device 420 through one or more internal leads 455 or through wireless connections. Patient-external sensors 442 may communicate with the patient-internal medical device 410 wirelessly. Patient-external sensors 446 may be coupled to the patient-external medical device 420 through one or more internal leads 457 or through a wireless link.

In an embodiment of the present invention using heart sound information along with ECG information, as will be further described below with reference to FIGS. 2 through 4, the patient-external medical device 420 includes a visual display configured to simultaneously display non-electrophysiological signals and ECG signals. For example, the display may present the information visually, as shown in FIG. 4. The patient-external medical device 420 may also, or alternately, provide signals to other components of the medical system 400 for presentation to a clinician, whether local to the patient or remote to the patient.

Referring still to FIG. 1E, the medical devices 410, 420 may be connected to one or more information acquisition devices 444, 448, such as a database that stores information useful in connection with the monitoring, diagnostic, or therapy functions of the medical devices 410, 420. For example, one or more of the medical devices 410, 420 may be coupled through a network to a patient information server 430.

The patient input/trigger devices 443, 447 are used to allow the patient to manually trigger and/or transfer information to the medical devices 410, 420. The patient input/trigger devices 443, 447 may be particularly useful for inputting information concerning patient perceptions, such as a perceived cardiac event, how well the patient feels, and other information not automatically sensed or detected by the medical devices 410, 420. For example, the patient may trigger the patient input/trigger device 443 upon perceiving a cardiac event. The trigger may then initiate the recording of cardiac and heart sound signals in the patient-internal device 410. Later, a clinician my trigger the patient input/trigger device 447, initiating the transfer of the recorded cardiac and heart sound signals from the patient-internal device 410 to the patient-external device 420 for display and diagnosis.

In one embodiment, the patient-internal medical device 410 and the patient-external medical device 420 may communicate through a wireless link between the medical devices 410, 420. For example, the patient-internal and patient-external devices 410, 420 may be coupled through a short-range radio link, such as Bluetooth, IEEE 802.11, and/or a proprietary wireless protocol. The communications link may facilitate uni-directional or bi-directional communication between the patient-internal 410 and patient-external 420 medical devices. Data and/or control signals may be transmitted between the patient-internal 410 and patient-external 420 medical devices to coordinate the functions of the medical devices 410, 420.

In another embodiment, patient data may be downloaded from one or more of the medical devices periodically or on command, and stored at the patient information server 430. The physician and/or the patient may communicate with the medical devices and the patient information server 430, for example, to acquire patient data or to initiate, terminate or modify recording and/or therapy.

The data stored on the patient information server 430 may be accessible by the patient and the patient's physician through one or more terminals 450, e.g., remote computers located in the patient's home or the physician's office. The patient information server 430 may be used to communicate to one or more of the patient-internal and patient-external medical devices 410, 420 to provide remote control of the monitoring, diagnosis, and/or therapy functions of the medical devices 410, 420.

In one embodiment, the patient's physician may access patient data transmitted from the medical devices 410, 420 to the patient information server 430. After evaluation of the patient data, the patient's physician may communicate with one or more of the patient-internal or patient-external devices 410, 420 through an APM system 440 to initiate, terminate, or modify the monitoring, diagnostic, and/or therapy functions of the patient-internal and/or patient-external medical systems 410, 420.

In another embodiment, the patient-internal and patient-external medical devices 410, 420 may not communicate directly, but may communicate indirectly through the APM system 440. In this embodiment, the APM system 440 may operate as an intermediary between two or more of the medical devices 410, 420. For example, data and/or control information may be transferred from one of the medical devices 410, 420 to the APM system 440. The APM system 440 may transfer the data and/or control information to another of the medical devices 410, 420.

In one embodiment, the APM system 440 may communicate directly with the patient-internal and/or patient-external medical devices 410, 420. In another embodiment, the APM system 440 may communicate with the patient-internal and/or patient-external medical devices 410, 420 through medical device programmers 460, 470 respectively associated with each medical device 410, 420. As was stated previously, the patient-internal medical device 410 may take the form of an implantable ITCS device. For purposes of clarity and understanding, further aspects of the present invention will be described in reference to an implantable ITCS device.

Figure 2:
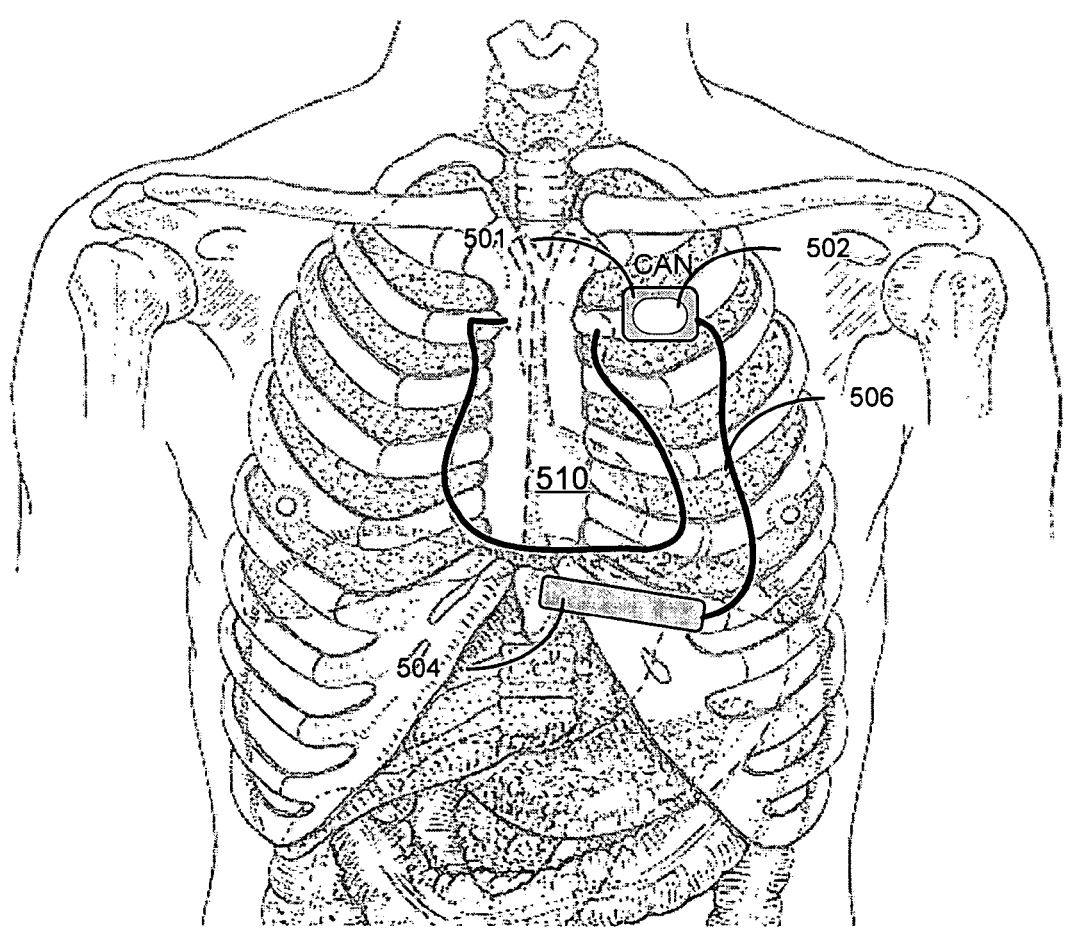
FIG. 2 is a diagram illustrating components of a transthoracic cardiac sensing and/or stimulation device including an audio sensor in accordance with an embodiment of the present invention.

In one configuration of an ITCS incorporating non-electrophysiological signal playback according to the present invention, as is illustrated in FIG. 2, electrode subsystems of an ITCS device are arranged about a patient's heart 510. The ITCS device includes a non-electrophysiological sensor, comprising an audio sensor 502, and an electrode subsystem 504 that includes at least one ECG electrode. The electrode subsystem 504 may include a number of electrodes used for sensing and/or electrical stimulation.

In various configurations, the electrode subsystem 504 may include a combination of electrodes. The combination of electrodes of the electrode subsystem 504 may include coil electrodes, tip electrodes, ring electrodes, multi-element coils, spiral coils, spiral coils mounted on non-conductive backing, screen patch electrodes, and other electrode configurations. A suitable non-conductive backing material is silicone rubber, for example.

The audio sensor 502 is positioned on the housing 501 that encloses the ITCS device electronics. In one embodiment, various portions of the housing 501 may be used as the audio sensor 502. For example, the active area of the audio sensor 502 may include a piezoelectric sensor useful as a pressure transducer, to sense pressure waves emanating from the heart. A signal independent of cardiac electrical activity, such as an acoustic signal of cardiac heart-sounds, an accelerometer signal, a blood sensor signal, or other non-electrophysiological sensor signal may be used in accordance with the present invention.

In another embodiment, the audio sensor 502 may be a subcutaneous sensor positioned on a lead, such as an accelerometer or microphone, used to detect heart sounds. The ITCS device, and/or a clinician may use the heart sounds together with rate, curvature, and other ECG information to discriminate normal sinus rhythm from electrical noise or potentially lethal arrhythmias such as ventricular tachycardia and ventricular fibrillation. Because the additional discriminating non-electrophysiological signal is correlated to the cardiac electrophysiological signals, this signal may provide information about a patient's rhythm state even in the presence of electrical noise.

A heart rate determined from the ECG signal may, for example, be analyzed along with heart sound information for diagnosis. High ECG heart rate detection along with normal rate heart sounds would indicate the presence of noise in the ECG signal. High ECG heart rate detection along with modified heart sounds would indicate a potentially lethal arrhythmia. It is noted that ECG morphology or other techniques could replace rate in the example above. It should also be noted that other sensor-derived signals could replace heart sounds. For example, impedance, pulse pressure, blood volume/flow, or cardiac accelerations could be used.

Various types of acoustic sensors may be used to detect heart sounds and utilized as the audio sensor 502. Examples of such acoustic sensors include diaphragm based acoustic sensors, MEMS-based acoustic sensors such as a MEMS-based acoustic transducer, fiber optic acoustic sensors, piezoelectric sensors, and accelerometer based acoustic sensors and arrays. These sensors may be used to detect the audio frequency pressure waves associated with the heart sounds, and may also be used to detect other non-electrophysiological cardiac related signals.

The presence of cardiac pulse, or heartbeat, in a patient is generally detected by palpating the patient's neck and sensing changes in the volume of the patient's carotid artery due to blood pumped from the patient's heart. A graph of a carotid pulse signal 810, representative of the physical expansion and contraction of a patient's carotid artery during two consecutive pulses, or heartbeats, is shown at the top of FIG. 3. When the heart's ventricles contract during a heartbeat, a pressure wave is sent throughout the patient's peripheral circulation system. The carotid pulse signal 810 shown in FIG. 3 rises with the ventricular ejection of blood at systole and peaks when the pressure wave from the heart reaches a maximum. The carotid pulse signal 810 falls off again as the pressure subsides toward the end of each pulse.

The opening and closing of the patient's heart valves during a heartbeat causes high-frequency vibrations in the adjacent heart wall and blood vessels. These vibrations may be heard in the patient's body as heart sounds, and may be detected by sensors, as described earlier. A conventional phonocardiogram (PCG) transducer placed on a patient converts the acoustical energy of the heart sounds to electrical energy, resulting in a PCG waveform 820 that may be recorded and displayed, as shown by the graph in the upper middle portion of FIG. 3.

Figure 3:
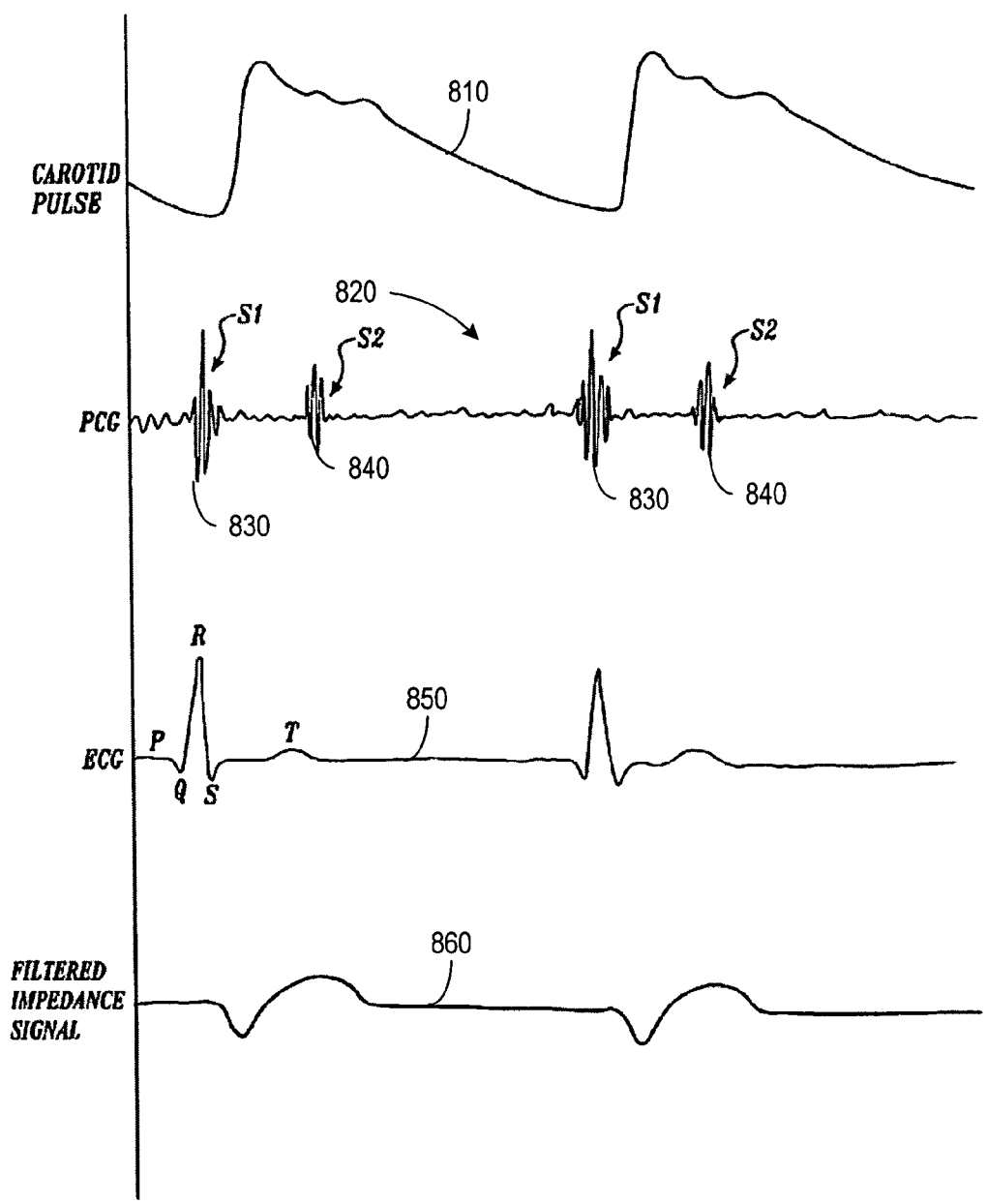
FIG. 3 is a pictorial diagram of a carotid pulse waveform, a phonocardiogram (PCG) waveform, an electrocardiogram (ECG) waveform, and a filtered transthoracic impedance signal for two consecutive heartbeats.
Figure 4:
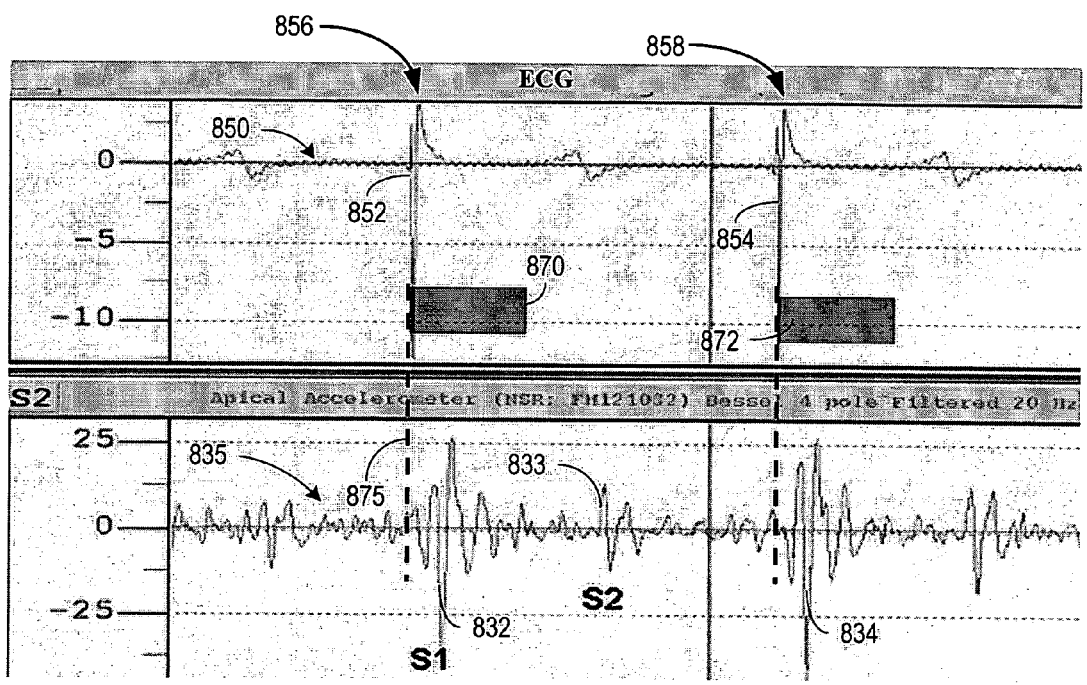
FIG. 4 is a graph illustrating two consecutive PQRS complexes and their associated accelerometer signals, and fiducial markers for correlation of the signals in accordance with an embodiment of the present invention.

As indicated by the PCG waveform 820 shown in FIG. 3, a typical heartbeat produces two main heart sounds. A first heart sound 830, denoted S1, is generated by vibration generally associated with the closure of the tricuspid and mitral valves at the beginning of systole. Typically, the heart sound 830 is about 14 milliseconds long and contains frequencies up to approximately 500 Hz. A second heart sound 840, denoted S2, is generally associated with vibrations resulting from the closure of the aortic and pulmonary valves at the end of systole. While the duration of the second heart sound 840 is typically shorter than the first heart sound 830, the spectral bandwidth of the second heart sound 840 is typically larger than that of the first heart sound 830.

An ECG waveform 850 describes the electrical activity of a patient's heart. The graph in the lower middle portion of FIG. 3 illustrates an example of the ECG waveform 850 for two heartbeats and corresponds in time with the carotid pulse signal 810 and PCG waveform 820 also shown in FIG. 3. Referring to the first shown heartbeat, the portion of the ECG waveform 850 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform representing repolarization of the ventricular muscle fibers is known as the "T" wave. Between heartbeats, the ECG waveform 850 returns to an isopotential level.

Fluctuations in a patient's transthoracic impedance signal 860 also correlate with blood flow that occurs with each cardiac pulse wave. The bottom graph of FIG. 3 illustrates an example of a filtered transthoracic impedance signal 860 for a patient in which fluctuations in impedance correspond in time with the carotid pulse signal 810, the PCG waveform 820, and ECG waveform 850, also shown in FIG. 3.

FIG. 4 is a graph illustrating two consecutive PQRS complexes in the ECG signal 850 and their associated non-electrophysiological components developed from an accelerometer signal 835. The graph of FIG. 4 is an example of the simultaneous display of heart sound information along with ECG information, such as would be displayed by the patient-external medical device 420 described with reference to FIG. 1E. It is understood that the heart sound information may be presented visually, as in FIG. 4, and/or may be broadcast as an audio signal.

As is illustrated in FIG. 4, an S1 heart sound 832 and an S1 heart sound 834 are, in general, closely time correlated with a QRS complex 852 and a QRS complex 854 respectively. Also illustrated is a correlation window 870 positioned by a fiducial point 875, such as the Q point of the QRS complex 852. The correlation window 870 illustrates a period of time where both ECG information and heart sound information from the same heartbeat are available. The S1 heart sound 832, an S2 heart sound 833, and the S1 heart sound 834 are illustrated as detected from an internally implanted accelerometer.

An ITCS device may be implemented to include signal processing circuitry and/or signal processing software as illustrated in FIGS. 1C and 1D. With continued reference to FIG. 4, signal processing may be used to correlate heart sounds, such as the S1 heart sound, with R-wave peaks or other QRS complex features, to allow selection of the correct signal (i.e. the cardiac ECG signal) after blind source separation or other separation technique has separated the ECG signal from various other signals.

Implantable cardiac system that store both ECG signals and non-electrophysiological signals, such as heart sounds, provide the clinician with a dual sensory review. For example, providing audio playback of the heart sounds during episode review of visual ECG signals would help the clinician assess rhythm types through both audio and video outputs. As advanced patient management systems are widely implemented, non-electrophysiological sensor information such as cardiac auscultations may become more important in assessing patient well-being, or in rhythm confirmation of stored episodes.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:
1. A medical system, comprising:
   a patient-implantable device, comprising:
      a housing;
      a plurality of electrodes coupled to the housing and configured for sensing cardiac electrical activity and electrical activity having an origin other than a heart;

detection circuitry provided in the housing and coupled to at least some of the plurality of electrodes, the detection circuitry producing electrical signals in response to the sensed electrical activity and a cardiac electrical signal in response to the sensed cardiac electrical activity;

a sensor configured to sense movement of the heart and produce a sensor signal in response to the sensed heart movement;

sensor circuitry provided in the housing and coupled to the sensor, the sensor circuitry configured to produce an audio signal in response to the sensor signal;

memory provided in the housing and coupled to the detection circuitry and sensor circuitry, the memory configured to store the audio signal and the cardiac electrical signal;

a controller provided in the housing and coupled to the memory, detection circuitry, and sensor circuitry, the controller configured to detect heart sounds from the audio signal, select the cardiac electrical signal from the electrical signals having an origin other than the heart based on temporal correlation of S1 heart sounds of the audio signal with QRS complexes of the cardiac electrical signal, discriminate between normal cardiac function and cardiac tachyarrhythmia based on the cardiac electrical signal and the audio signal, and provide an output based on the discrimination between normal cardiac function and cardiac tachyarrhythmia, the controller configured to open a correlation window based on a cardiac cycle feature fiducial point of the cardiac electrical signal to correlate heart sounds with cardiac cycle features of the same heart beat over a plurality of cardiac cycles, and to discriminate between normal cardiac function and cardiac tachyarrhythmia based on temporal correlation between heart sounds and cardiac cycle features over the plurality of cardiac cycles; and communications circuitry provided in the housing and coupled to the controller, the communications circuitry configured to telemeter the cardiac electrical signal and the audio signal; and a patient-external device comprising:

patient-external communications circuitry configured to receive the cardiac electrical signal and the audio signal telemetered from the patient-implantable device;

a storage media to store the cardiac electrical signal and the audio signal telemetered from the patient-implantable device; and a user interface coupled to the patient-external communications circuitry, the user interface configured for providing a visual output representative of the cardiac electrical signal and an audio output representative of the audio signal.

2. The medical system of claim 1, wherein discrimination between normal cardiac function and cardiac arrhythmia comprises discrimination between normal heart rate and arrhythmic heart rate, wherein:

the controller indicates the heart rate to be normal and the cardiac electrical signal subject to electrical noise if the cardiac electrical signal indicates high heart rate and the audio signal indicates normal heart sounds; and the controller indicates the heart rate to be arrhythmic if the cardiac electrical signal indicates high heart rate and the audio signal indicates modified heart sounds.

3. The medical system of claim 1, wherein:

the controller determines the cardiac function to be normal if the cardiac electrical signal indicates abnormal cardiac morphology and the audio signal indicates normal heart sounds; and the controller determines the cardiac function to be arrhythmic if the cardiac electrical signal indicates abnormal cardiac morphology and the audio signal indicates modified heart sounds.

4. The medical system of claim 1, wherein discrimination between normal cardiac function and cardiac arrhythmia comprises identification of electrical noise and wherein the controller indicates the presence of noise if the cardiac electrical signal indicates high heart rate and the audio signal indicates normal heart sounds.

5. The medical system of claim 1, wherein discrimination between normal cardiac function and cardiac arrhythmia comprises discrimination between normal sinus rhythm and one or both of ventricular tachycardia and fibrillation based on temporal correlation of cardiac sound features of the audio signal with features of the cardiac electrical signal.

6. The medical system of claim 1, further comprising a human input, wherein production of the audio signal by the sensor circuitry is initiated based on triggering of the human input.

7. The medical system of claim 1, wherein the output comprises transmission of an indication of the discrimination between normal cardiac function and cardiac arrhythmia by the communications circuitry to the patient-external communications circuitry and storage of the indication in memory.

8. The medical system of claim 1, wherein the sensor is disposed on a lead connected to the patient-implantable device.

9. The medical system of claim 1, wherein the sensor is at least partially contained within the housing, and the housing and the plurality of electrodes form a rigid unitary structure.

* * * * *